United States Patent [19]

DeWitt et al.

[11] Patent Number: 4,734,941

[45] Date of Patent: Apr. 5, 1988

[54] FLUSHABLE URINE CONDUCTING APPLIANCE

[76] Inventors: Elizabeth M. DeWitt, 1616 McCay Ave., Boothwyn, Pa. 19061; Richard Grime, P.O. Box 186, Royersford, Pa. 19468

[21] Appl. No.: 48,926

[22] Filed: May 13, 1987

[51] Int. Cl.[4] .......... A47K 11/00

[52] U.S. Cl. .......... 4/144.4; 4/144.2; 4/144.3

[58] Field of Search .......... 4/452, 144.1, 144.2, 4/144.3, 144.4, 451, 661

[56] References Cited

U.S. PATENT DOCUMENTS

| | | | |
|---|---|---|---|
| 1,407,872 | 2/1922 | Lacy | 4/144.2 |
| 2,878,486 | 3/1959 | Bartlett et al. | 4/144.2 |
| 3,475,767 | 11/1969 | Friesen et al. | 4/452 |
| 3,546,716 | 12/1970 | Laumann | 4/452 |
| 3,591,870 | 7/1971 | Friesen | 4/144.2 |
| 3,613,122 | 10/1971 | Gross et al. | 4/144.4 |
| 3,654,064 | 4/1972 | Laumann | 4/451 X |
| 3,763,502 | 10/1973 | Laumann | 4/452 |
| 3,964,111 | 6/1976 | Packer | 4/144.4 |

*Primary Examiner*—Henry K. Artis

*Attorney, Agent, or Firm*—Eugene E. Renz, Jr.

[57] ABSTRACT

A flushable urine conductive appliance comprising a flexible layered sheet adapted to be folded for positioning between the legs of a female to direct urine to an appropriate receptacle including at least an inner layer formed from a fibrous or non-fibrous sheet adapted for rapid disintegration of structural integrity in contact with water, and intermediate layer formed from at least one continuous film of water-soluble polymer, and an outer layer formed from at least one fibrous or non-fibrous sheet and capable of rapid disintegration of structural integrity when in contact with water.

4 Claims, 2 Drawing Sheets

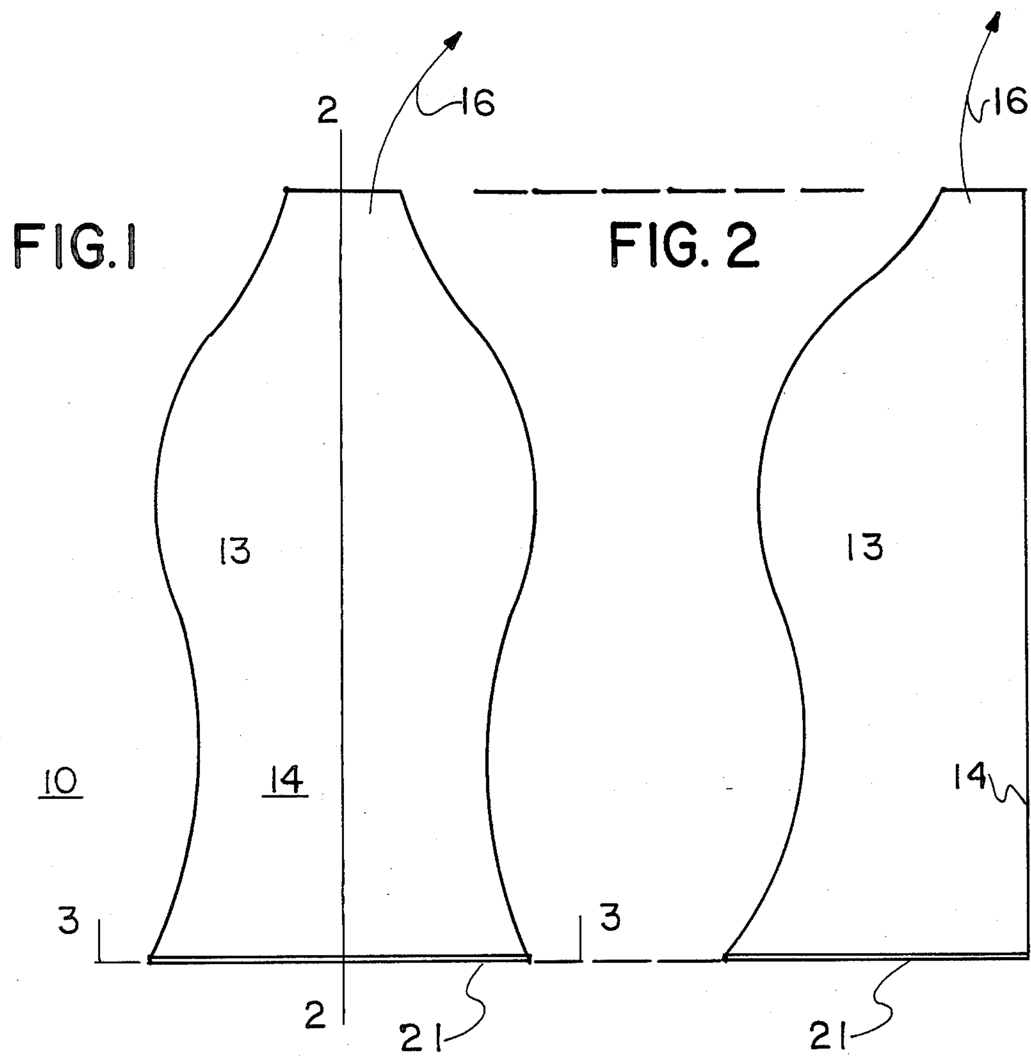
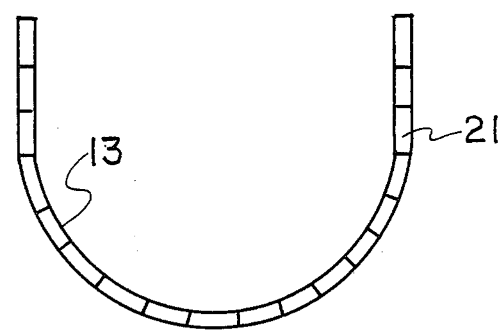
FIG. 3

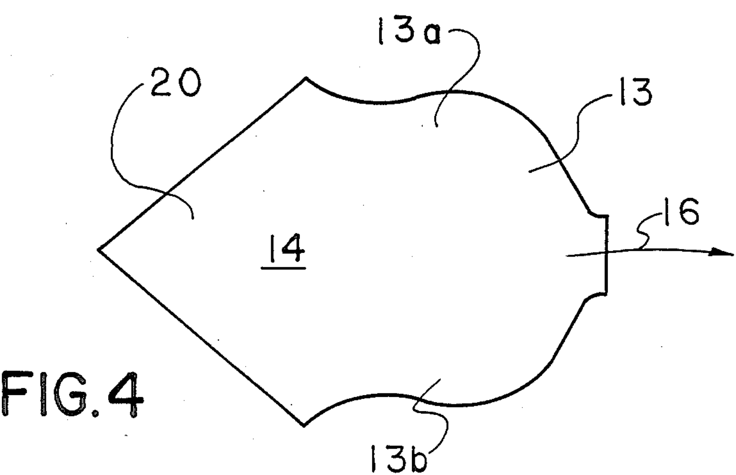
FIG. 4
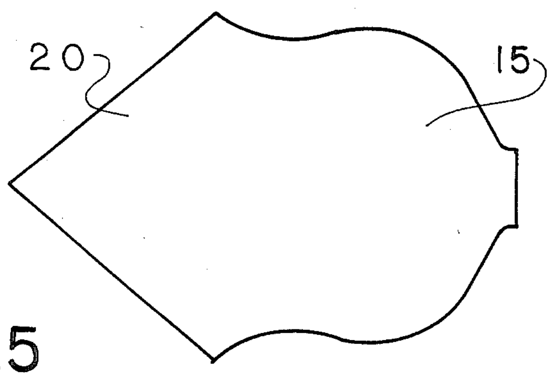
FIG. 5
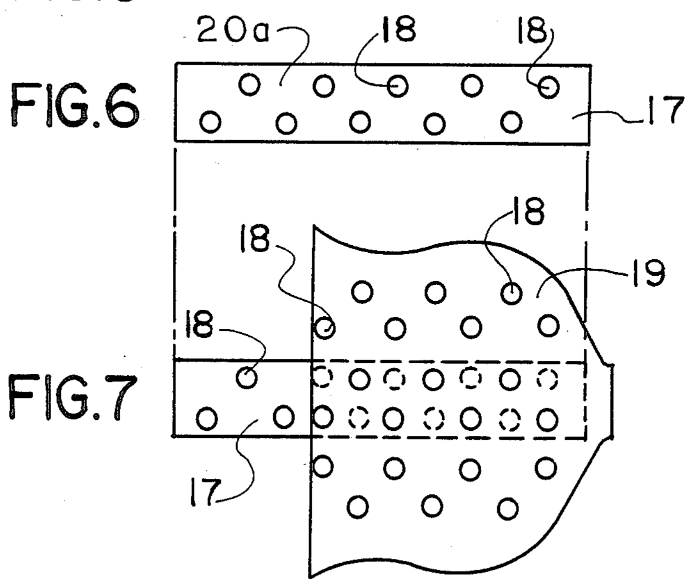
FIG. 6
FIG. 7
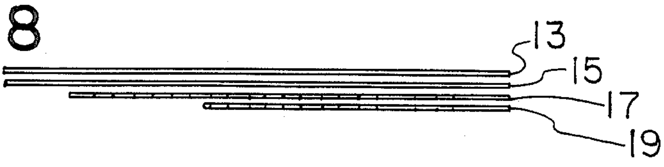
FIG. 8
FIG. 9

FLUSHABLE URINE CONDUCTING APPLIANCE

FIELD OF THE INVENTION

The present invention relates to disposable products which are suitable for use by females, particularly in public restroom facilities.

BACKGROUND OF THE INVENTION

It is a well-established fact that women's restrooms, in general, and women's toilet facilities, in particular, leave a great amount to be desired in the matter of cleanliness and sanitation. Even when the facilities are cleaned on a frequent basis, only a short time is needed for unsanitary and unclean conditions to be re-established. Moreover, the discovery of a soiled restroom tends to result in additional careless use and increased soiling. When urinating in one of these facilities, many women try to avoid contact with the bowl and/or seat. Methods for avoiding contact include using toilet seat covers, toilet tissue in large quantities, or by straddling the bowl. These methods are difficult, if not physically impossible for some women. Moreover, the methods are messy, cumbersome, and of clearly questionable effectiveness. Consequently, women are becoming much more concerned about potential health hazards associated with coming in contact with unsanitary toilet seats. Rapid increase in sexually transmitted diseases has further compounded this concern. Whether or not it is a warranted concern, many women would readily endorse a satisfactory alternative which would eliminate the need to take a sitting or crouching position over a toilet bowl while urinating.

Other potential uses for the invention might include camping or international travel where toilet facilities are either different than normal or non-existent altogether. Because of these many concerns, many women significantly alter their own travel schedules to avoid unsanitary facilities, often at inconvenience to themselves and others.

DESCRIPTION OF THE PRIOR ART

A number of products have been proposed to assist in the sanitary disposal of urine, particularly for women when they are in an environment which is not itself sanitary. Examples of these are shown in Bortle U.S. Pat. No. 4,296,502 which describes a self-packaging urine conduit. This device is manufactured from lightweight plastic or rubber and is preferably biodegradable so that it may be disposed of properly in a trash bin.

Another device of this nature is disclosed in Kutsche U.S. Pat. No. 2,734,198 in which a urinal is formed from a flexible material such as paper, cardboard, plastic or rubber. The device is designed to hold the urine until it is disposed of in the water closet.

Diaz U.S. Pat. No. 4,305,161 discloses a waterproof, disposable bag which has a fold at its upper end and a rigid wish-bone shaped frame to facilitate use by women during urination. The frame is reusable, assuming it can be properly sanitized.

A similar device for a related situation is shown in Garland U.S. Pat. No. 3,572,318 which describes a urine specimen collection aid. This device is made from a foldable sheet material which forms into a funnel.

Other mechanical aids include the urinal device shown in Li U.S. Pat. No. 4,023,216 which includes a portion of a material which is truly disposable along with a portion which is not disposable. Pate U.S. Pat. No. 4,490,863 describes a hand-held urine receiver which permits its use by females with an adaptor insert.

Beebe et al U.S. Pat. No. 3,542,028 describes a flushable, sanitary napkin which, of course, is not adequate for the present concern, but which does describe the difficulty contemplated by those skilled in the art in providing an easily flushable device. This problem is partially remedied in Parrish U.S. Pat. No. 3,521,638 in which water-sensitive cellulose derivative fibers are employed. Laumann U.S. Pat. No. 3,654,064 uses a water insoluble layer which is thin enough to be torn apart during flushing or other disposal processes. Nevertheless, the device itself is not water soluble or dispersible. One form of an insoluble film, such as a polyolefin film, which is useful for increasing capillary action, is described in Thomas et al U.S. Pat. No. 4,535,020.

It is clear from a reading of the foregoing prior art, however, that none of the attempts which have been made to this date directly address the problem of having a flushable, totally disposable urine-conductive appliance which is useful by women under a wide variety of circumstances and which does not present problems of sanitation or disposal.

SUMMARY OF THE INVENTION

In spite of the foregoing deficiencies of the prior art, it has now been discovered that a truly flushable urine-conducting appliance for use by women can be provided in the following manner. Specifically, the device comprises a flexible layered sheet which is adapted to be folded for positioning between the legs of a female to direct urine to an appropriate receptacle without contacting highly sensitive areas of the body. The layered sheet includes at least an inner layer which is formed from a fibrous or non-fibrous sheet adapted for rapid disintegration of its structural integrity when it is placed in contact with water. The device also has at least one intermediate layer which is formed from a continuous film of water soluble polymer. Finally, the device has at least one outer layer which is formed from a fibrous or non-fibrous sheet which is also capable of rapid disintegration of its structural integrity when in contact with water. In the dry condition prior to use, the layered sheet provides an initial barrier to disintegration for a short period of time prior to disposal of the device in the appropriate receptacle. For convenience, an incidental wiping tissue may be included.

BRIEF DESCRIPTION OF THE DRAWINGS

The objects of the present invention and the various features and details of the operation and construction thereof are hereinafter more fully set forth with reference to the accompanying drawings, wherein:

FIG. 1 is a top view of a preferred embodiment according to the present invention, as it will be used;

FIG. 2 is a side view taken along lines 2—2 of FIG. 1;

FIG. 3 is a sectioned end view taken along lines 3—3 of the device shown in FIG. 1;

FIG. 4 is a top view of the preferred embodiment in a flat position;

FIG. 5 is a top view of the device shown in FIG. 4 with the top layer removed;

FIG. 6 is the device shown in FIG. 5 with the second layer, or intermediate layer, removed;

FIG. 7 is a top view of the device with the layer shown in FIG. 6 present;

FIG. 8 is a side view of the preferred embodiment showing the layers separated from one another; and FIG. 9 is a side view of the preferred embodiment formed together as a product to be marketed.

DETAILED DESCRIPTION OF THE PREFERRED EMBODIMENT

As shown in FIG. 1, the device is shown in the top view looking down on the device as it is held between the two hands of the user. As is clear from the foregoing description, the user will be a female desiring to void urine into an appropriate receptacle without having to contact anything which is unsanitary or unclean. As the woman faces the toilet, she is to lift the toilet seat and stand close to the bowl. The appliance is grasped on each side, with thumb and middle finger approximately mid-way down the length and behind the flaps or splash guards. Spreading the legs, the protective lip is held snugly against the pubic area at the perineum. The forefingers are then used to gather the splash guards together to form a scoop or funnel shape through which the urine is directed into the toilet bowl or other suitable receptacle. The used device is flushed down the toilet. The aforementioned wiping tissue is available for use as desired.

As shown in FIG. 1, the device is folded into a shape somewhat like a scoop or funnel to permit the conduction of urine into an appropriate receptacle. The urine impacts upon the top sheet 13 such as at 14 and flows down the scoop-like device out the end in the direction shown by arrow 16. At the end which is close to the person's body, a roll 21 forms a protective lip which when pressed firmly against the body, provides a water tight seal.

The top or inner layer 13 is formed from a fibrous or non-fibrous sheet which is adapted for disintegration of structural integrity after a minimum predetermined time when contacted with water or other fluids such as urine. A preferred product from which the top or inner layer 13 is prepared is tissue paper. Other material may be used, such as thin films or non-fibrous sheets. Most preferred is a tissue paper which has been treated with a water-soluble polymer so as to provide dry structural integrity. Suitable polymers such as polyvinyl alcohol may be impregnated into this top sheet to provide the needed dry structural integrity while allowing complete solubility of the sheet when the device is discarded into the toilet bowl or other disposal container. It is desirable that the water-soluble polymer will not dissolve in water or urine or the fluids in the receptacle before about thirty seconds or slightly longer. In addition to tissue paper, other paper grades as well as water soluble resins, cellulose ethers, gelatine, synthetic polymers of ethylene oxide, methyl cellulose or polyvinyl alcohol, and natural substances such as starch, gum tragaranth and various alengates may be used to form the sheet.

Prior to use, the top layer 13, when it is flat, has a general shape as shown in FIG. 4. On the right side of the device shown in FIG. 4 is the discharge end as shown by arrow 16. The opposite end 20 is shown in triangular shape but may be any shape which is suitable for rolling up to form the end barrier 21 as shown in FIG. 9. The two sides of the layer 13, areas 13*a* and 13*b*, may extend outward a short distance from the center in this embodiment, so as to provide an area which may be folded over the thumbs when they hold the device in the scoop shape for use. Even if areas 13*a* and 13*b* are not used, each side of the sheet may be grasped by the thumb below and the forefinger above the sheet 13, rotation of the sheet 13 helps to protect against splashing on the user's hands.

Directly below the top layer 13 is at least one intermediate layer 15 which is formed from a continuous film of water-soluble polymer or hydrated gel. Any of the above described sheet forming materials may be used. The purpose of this layer 15, which is shaped like the top layer 13 but may be sized slightly smaller, is to act as a barrier as the urine penetrates the top tissue layer so that the urine will continue to be directed to the discharge end at arrow 16 and into the appropriate receptacle. The water-soluble polymer acts as a barrier for a short period of time, say up to between thirty seconds and as much as sixty seconds, so that the flow of urine does not penetrate entirely through the device. Once the device has been discarded into the toilet bowl or other receptacle, rapid dissolution of the water-soluble polymer is accomplished and the device continues to be totally disposable via flushing or other means.

Any water-soluble polymer which does not have instantaneous solubility in water but which can act as a temporary barrier to water flow for at least fifteen to thirty seconds may be used. Sheets formed from hydroxyethyl cellulose polymers are admirably suited for use in the intermediate layer. Also, polyethylene oxide polymers, hydrated gels and some organic starches or other materials as listed above, may also be employed to make water-soluble films or sheets. It is not necessary that the layer 15 be particularly thick, but the thickness should be sufficient to provide a temporary barrier to prevent the urine from passing through to the next layer below. The barrier layer 15 also gives some dry structural support to the device.

The final layer which forms a part of the device of this invention is an outer layer 19 which is formed from a fibrous or non-fibrous sheet and which is capable of rapid disintegration of its structural integrity when in contact with water. It may be constructed from paper or other fibrous materials which are capable of rapid disintegration when subjected to water and the action of flushing in a toilet. The other materials may also be used for this layer. The purpose of the layer 19 is to provide structural integrity in the dry condition to the device as constructed and to provide a barrier between the user and the water soluble continuous film 15. This outer layer may comprise a third sheet formed from paper or other fibrous material, or non-fibrous materials, in the shape shown by either top layer 13 or intermediate layer 15.

In its simplest form, this three-layer device would be quite suitable for the purposes of this invention. In a preferred embodiment, an additional feature is added to assist in accomplishing the total disintegration of the structural integrity of the device when it is in contact with water. Specifically, as shown in FIG. 6, a strip of fibrous or non-fibrous material 17 is placed below the intermediate layer 15 to provide an area about which the folded portions can be centered. Holes 18 are placed in the outer layer 17 so as to permit water to reach the underside of intermediate layer 17 more rapidly when the device is dropped into the toilet bowl. A second outer layer 19 is provided, again with holes 18, in a slightly different location so as to give additional structural integrity to the device in the dry state prior to its use. This additional outer layer 19 is shaped to conform to the front portion of intermediate layer 15 and inner layer 13, as shown in FIG. 7, but is shorter than, for example, inner layer 13.

As shown in FIG. 8, the inner layer 13 is above the intermediate layer 15 and approximately the same size. Outer layer 17, shown as a strip in FIGS. 6 and 7 is nearly as long as intermediate layer 15 and is positioned directly below it and centered along the center of layers 13 and 15. Below layer 17 is layer 19 of the shape shown in FIG. 7. The ends 20 of layers 13, 15 as well as end 20*a* of layer 17 are then rolled into a barrier 21 which functions to prevent fluid flow in the wrong direction during use of the device. In an alternative embodiment, the lip or barrier 21 may be designed to break away, such as by a tearing action after use, so that more rapid disintegration in the disposing operation will take place.

As a further aid to disintegration and flushability of the product after deposition in the toilet bowl, the intermediate layers are not fastened to each other or to the outer layers in any way, but are simply captured by the two outer layers. This is accomplished by making the outer layers larger than any intermediate layers and then lightly and intermittently bonding the outer layers to each other at the margin which extends beyond the intermediate layers. These bonds are intended to very quickly be destroyed by water, allowing all layers of the product to separate.

During, use the greater portion of the bonded margin is not subject to wetting and will maintain its integrity during this critical period.

Gluing, crimping or any other method of bonding can be used, so long as the bonds are quickly destroyed by water.

While a particular embodiment of the invention has been illustrated and described herein, it is not intended to limit the invention and changes and modifications may be made therein within the scope of the following claims.

What is claimed is:

1. A flushable urine conductive applicance, comprising a flexible layered sheet made solely from water disintegratable material and adapted to be folded for positioning between the legs of a female to direct urine into an appropriate receptacle, said layered sheet including an inner layer capable of rapid disintegration of its structural integrity during urination, an intermediate layer formed from at least one continuous film of a water-soluble polymer selected from hydroxyethyl cellulose polymers, polyvinyl alcohol, polyethylene oxide polymers, hydrated gels and organic starches, to delay urine penetration for at least 30 seconds, and an outer layer including a strip having a substantial length to width ratio and positioned to have its length extending in the direction of intended fluid flow, said outer layer being capable of rapid disintegration of its structural integrity when in contact with water.

2. The device of claim 1, wherein said fibrous sheet is treated with a watersoluble polymer to provide dry structural integrity thereof.

3. The device of claim 1, wherein said outer layer includes a second sheet shaped generally to conform to the shape of at least the discharge end of said inner layer.

4. The device of claim 1, wherein said outer layer has a plurality of open areas to permit rapid fluid access to the inner layer when the device is placed in contact with water so as to increase the rate of disintegration of the structural integrity of the device in contact with water.

* * * * *